United States Patent [19]

Roberts

[11] 4,323,299

[45] Apr. 6, 1982

[54] WIDE FIELD SPECULAR SCANNING DEVICE

[76] Inventor: Calvin W. Roberts, 160 E. 88th St., New York, N.Y. 10028

[21] Appl. No.: 165,568

[22] Filed: Jul. 3, 1980

[51] Int. Cl.³ .......................... G02B 21/06; A61B 3/12
[52] U.S. Cl. ...................................... 350/91; 351/14; 351/16
[58] Field of Search .................... 350/91, 271; 351/14, 351/16

[56] References Cited

U.S. PATENT DOCUMENTS

| | | | |
|---|---|---|---|
| 3,518,014 | 6/1970 | Weber | 350/91 X |
| 3,547,512 | 12/1970 | Baer | 350/91 X |
| 4,170,398 | 10/1979 | Koester | 351/16 X |

Primary Examiner—F. L. Evans
Assistant Examiner—Matthew W. Koren
Attorney, Agent, or Firm—Arthur B. Colvin

[57] ABSTRACT

The present invention relates to a wide field specular scanning device, especially intended for the examination under magnification of a selected area within the cornea of the eye. The device includes a specular microscope incorporating a converging lens and an objective lens or a group or series of lenses performing the functions thereof. A beam of light from a light source is passed through the lenses of the microscope into the cornea of the subject through a reciprocating or oscillating mask or plate having a first slit to one side of the optical axis of the microscope through which the beam is passed and a second slit to the opposite side of said axis a predetermined distance from the first slit through which the reflected beam transmitted backward through the microscope is passed through a magnifying lens or other device either for direct observation or onto a screen or photo-sensitive surface. By oscillating the mask at a rate which is above the image retention rate of the eye, the observer may derive an accurate impression of a selected area within the cornea of the eye. A particular advantage of the device is that the image is of high contrast and only a minimal quantity of stray light fractions are incorporated in the image.

9 Claims, 2 Drawing Figures

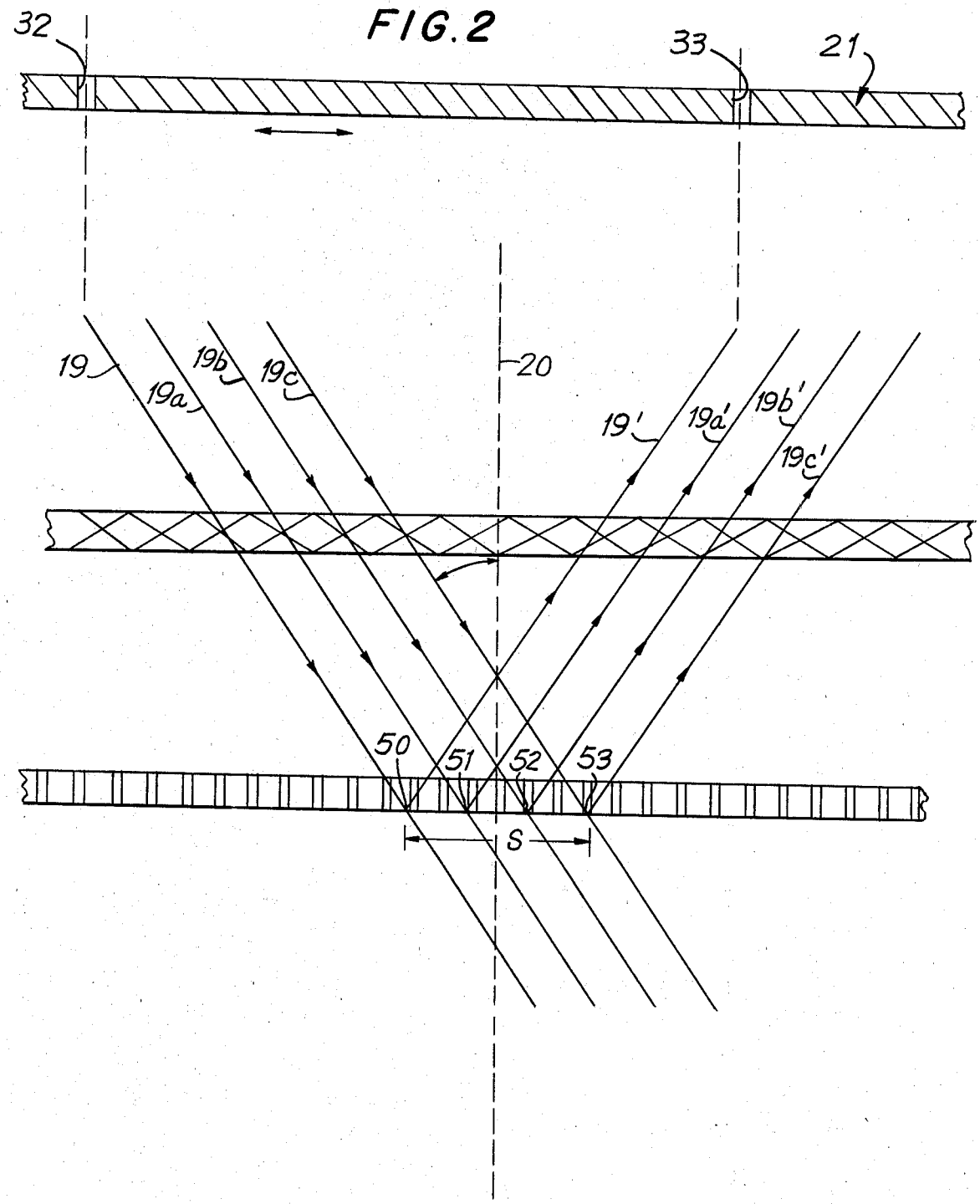

WIDE FIELD SPECULAR SCANNING DEVICE

BACKGROUND OF THE INVENTION

1. Field of the Invention

The present invention is in the field of optical devices and is directed more particularly to a specular microscope having a wide field scanning device intended particularly for the examination under magnification of a selected area within the relatively transparent cornea of the eye.

2. Prior Art

Recent studies have demonstrated the importance of being able accurately to inspect the cellular structure within the cornea of the eye of a subject. More particularly, the cornea is comprised of three transparent layers, namely the epithelium, stroma, and the endothelim. It has been determined that the cellular structure, particularly of the endothelium, is of particular significance in respect to performing corneal transplant operations since it is these cells which are responsible for maintaining corneal transparency. By careful examination of such layer, it is now possible to predict whether a particular donor cornea will result in a successful corneal transplant.

Furthermore, the ability to make a detailed inspection of the cellular structure of a wide area of the endothelial layer serves as an excellent diagnostic tool to determine various diseases of the eye for subsequent treatment.

In order for the physician to obtain an accurate indication of the endothelial cellular structure, it is necessary that a relatively wide area of the endothelial layer be inspected.

Where only a narrow region is able to be inspected, no spatial arrangement of the endothelial layer as a whole is possible, furthermore statistical analysis from multiple small fields is wrought with sampling errors.

Additionally, as noted since the cornea is comprised of a series of transparent layers, the image which may be derived utilizing conventional optical systems, is of extremely low contrast, since the observed image consists not only of light reflected from the surface sought to be examined, but also from light reflected or scattering from adjacent and intermediate reflective objects within the cornea.

Attempts have been made to devise optical apparatus which will enable corneal inspection of a relatively wide area. By way of example, reference is made to U.S. Pat. Nos. 3,547,512 of Dec. 15, 1970 and 4,170,398 of Oct. 9, 1979.

The devices of the subject patents while effective in a measure to permit corneal inspection of desired layers, comprise extremely complex optical and mechanical arrangements resulting in cumbersome and exceedingly expensive devices well beyond the financial capabilities of individual practioners and even of most medical institutions. Further by virtue of the complexity of the devices, it is mandatory that the same be operated by highly skilled technicians.

SUMMARY OF THE INVENTION

The present invention may be summarized as directed to a wide field specular microscope especially adapted for clinical studies of the corneal endothelium of the eye but also useful in visualizing structures within the stromal and epitheliul layers. Briefly, in accordance with the invention, there is provided an essentially conventional specular microscope including a converging and an objective lens or combination of lenses functioning in the manner of converging and specular lens groups. An illuminating means is provided for directing a light beam through the converging and objective lenses and into the interior of the cornea, the illuminating means admitting light to the specular microscope to one side of the optical axis thereof. Means are provided to the opposite side of the optical axis for inspecting the reflection of the light beam projected by the illuminating means, such observing means including a magnifying lens either alone or in conjunction with a screen or photo-sensitive plate. The device is characterized by the interposition between the illuminating means and the receiving or magnifying means of a mask which is opaque and is provided with a spaced pair of elongate but narrow slits, the mask being oscillated or reciprocated in a direction normal to the optical axis and the lengthwise dimension of the slits. The width of the slits and the spacing of the slits and their coordination with the specular device is so constructed and arranged as to illuminate, as a result of focusing of the microscope through one of said slits, an essentially planar area within the cornea which is scanned by the beam. The reflected light components which are received and passed through the opposite slit provide relatively high contrast images of the band which is scanned by the beam of illumination projected through the first slit. Due to the rapid oscillation of the mask, there is thus made observable, an accurate replica of a planar area within the cornea of the eye.

Accordingly, it is an object of the invention, to provide a wide field specular scanning device for the examination under magnification of a selected area and particularly a selected planar area within the cornea of the eye.

A further object of the invention is the provision of a device of the type described wherein the image resulting from the scanning procedure is of high quality and high contrast being substantially free of stray reflected light.

A further object of the invention, is the provision of a device of the type described which is of relatively simple construction and hence inexpensive to manufacture and easy to use.

Still a further object of the invention is the provision of a device of the type described wherein, unlike scanning devices heretofore known, the transmitted beam provided by the illuminating means and the reflected beam deriving from the target are passed through the same optical apparatus or lens system, thereby greatly simplifying the device and increasing the accuracy and contrast of the resultant image.

In order to obtain these objects and such other objects as may appear herein or be hereinafter pointed out, reference is made to the accompanying drawings in which:

FIG. 2 is an enlarged diagramatic view of the transmitted and reflected light beams demonstrating the manner in which a wide area of the endothelium may be viewed.

Figure 1:
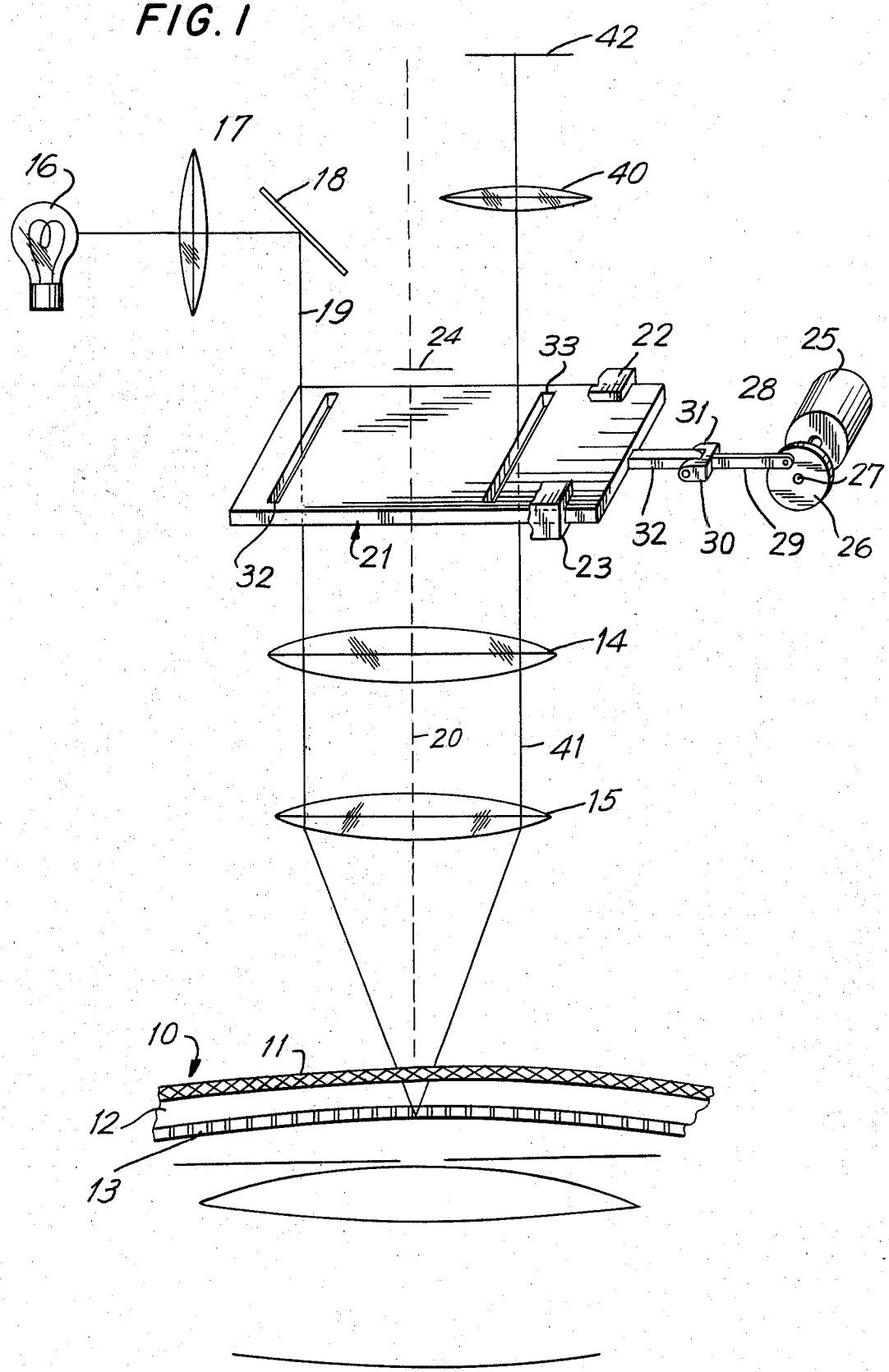
FIG. 1 is diagramatic or schematic illustration of an optical scanning apparatus in accordance with the invention.

Turning now to the drawings and particularly FIG. 1 thereof, there is disclosed a diagramatic or schematic representation of an optical scanning device particularly adapted to an inspection and examination of a focal plane within the cornea of the eye. As seen in FIG. 1, the cornea 10 is comprised of an outer or epithelium layer 11, a central or stroma layer 12, and an inner or endothelium layer 13. Each of the noted layers of the cornea is essentially transparent. Thus, unlike the typical situation where a specific focal plane desired to be examined can be strongly illuminated and the microscope focused on the illuminated area, the examination of a cornea presents unique problems in that the adjacent areas or boundaries do not present sharply contrasting optical images. Under such circumstances any further dilution of the contrast of the image obtainable, as by the reflection of stray light, will degrade the image to the point where the resolution of useful detail is impossible to the observer.

It is the function of the instant device to maximize image contrast by assuring that the light impinging upon the screen or photo-sensitive surface which is reflected from the plane sought to be examined is relatively undiluted by stray reflected light. To this end there is provided a specular microscope which in simplified form and for purposes of illustration only, is comprised of a converging lens 14, and an objective lens 15.

Illumination is derived from a light 16 such as an xenon arc or similar source. A collimating lens 17 is interposed between the light source 16 and a mirror or prism member 18 which functions to direct the light beams from the source of illumination into the microscope in a direction or beam 19 which is essentially parallel to the optical axis 20 of the microscope. The light beam 19 is reflected downwardly through a mask member 21 comprising a thin metal or like opaque plate which is disposed perpendicular to the optical axis 20. The mask or plate 21 is guided for a cyclical or reciprocal movement in the noted perpendicular plane as by guideway portions 22, 23 which slideably support the plate while guiding the same in the noted perpendicular plane.

Means are provided for oscillating the plate transversely in the direction of the arrow 24. In the representation of FIG. 1, the means for inducing oscillation comprises an electric motor 25 carrying a drive plate 26 affixed to the drive shaft 27 of the motor, the plate including an eccentric pin 28. A rocker arm 29 is affixed to the pin 28 pivotally at one end, the opposite end 30 of the arm 29 being pivotally secured at 31 to a link arm 32 extending from the mask 21. As will be evident from the foregoing description, when the motor 25 rotates, the plate or mask 21 will be caused to oscillate in a plane normal to the optical axis 20 at a rate which is a function of the speed of the motor 25. As will be apparent from the preceding description, the specific assembly selected to induce oscillation of the plate is illustrated by way of example only and in practice it may be preferable to connect the plate 21 to be armature of a solenoid fed with an alternating current, the frequency of which may be varied in accordance with the desired oscillating frequency of the mask.

The mask 21 is provided with a spaced pair of slits namely slit 32 and slit 33, the said slits being disposed to opposite sides of the optical axis 20. The slit 32 defines the width of the illuminating beam and the slit 33 allows passage of the reflected light from the planar area to be viewed, with a minimum of undesired reflections from other areas within the cornea. By way of illustration and without limitation the slits may have a transverse dimension of 1 millimeter and may be disposed between 8 to 10 millimeter to opposite sides of the optical axis 20. The oscillating apparatus may be arranged, illustratively, to induce the slits to a lateral excursion of between 5 to 7 millimeters and the slits may be oscillated at a speed of from 500 to 1,000 cycles per second. While the oscillating speed of the mask is not critical to the successful operation of the device, it is preferable that the oscillation be effected at a speed above the image retention speed of the eye of the viewer where the image is to be directly observed. The oscillating speed of the mask is less critical where the image is to be photographically reproduced.

The device includes a magnifying lens 40 positioned to focus the image of the reflected beam 41 on a screen 42 which may comprise a photo-sensitive plate or the input surface of an image intensifier tube.

Turning now to the view of FIG. 2, it will be perceived from the diagramatic representation thereof, that the beam of light 19 (which though illustratively shown as a line has a width determined by the width of slit 32) emerging from slit 32 can be focused by the lenses 14, 15 on to a planar area 50 along the surface S which is intended to be examined. The focused beam impinging on planar area 50, the transverse extent of which of course is dependent on the slit width, will be reflected from said point along beam line 19' when it will be bent vertically by the microscope lenses 15, 14 to correspond with the optical axis 20, passing outwardly through slit 33 and through magnifying device or eye piece 40 for examination, or alternatively onto a screen or photo-sensitive surface 42. A second line 19a is representative of the beam permitted to pass through slit 32 and lenses 14, 15 after the said slit 32 has been shifted an increment to the right when viewed in the orientation of FIG. 2. As will be seen, the beam 19a will impinge upon surface S along the essentially planar area represented by the reference numeral 51. The reflected beam 19a' eminating from the surface S will in turn be reflected in a direction parallel to the optical axis 20 and pass upwardly through slit 33 which has been moved concomitantly to the right corresponding to the rightward movement of the slit 32. With the oscillatory movement noted, beams 19b and 19c are sequentially projected against surface S at points 52 and 53 with reflected beams 19b' and 19c' passing outwardly through the slit 33. Since the mask 21 is rapidly oscillating at a speed which is beyond the image retention period of the eye, an observer looking at screen 42 will see an image thereon apparently corresponding to the entire width of the area S even though in actuality at any given time the real image actually impinged against surface 42 will be comprised of a small strip corresponding to the width of the beam which is at that given instant passing downwardly through slit 32 and upwardly through slit 33.

As will be understood from the arrangement described and disclosed, there is provided a simple relatively inexpensive specular microscope device of a unique type which will permit the examination of a planar area within the cornea of the eye in great detail and with minimal loss of contrast from spurious or unwanted reflections from within the cornea. The device of the instant invention permits the examination of a planar area within the cornea at any given time, many times the width of the slit 32, the width of such area being defined by the amplitude of the sweep of the mask 21 within the confines of the dimensions of the lens system 14, 15.

As will be apparent to skilled workers in the art, who have been familiarized with the instant disclosures, numerous variations particularly of a mechanical nature may be made without departing from the spirit of the present invention. By way of example and in addition to variations in the dimensional details given for purposes of compliance with the patent laws, the optical details of the microscope may be modified as may the mechanical means employed for oscillating the mask 21. Accordingly, the invention is intended to be broadly construed within the scope of the appended claims.

Having thus described my invention, what I claim as new and desire to secure by Letters Patent of the United States is:

1. A specular microscope having wide field scanning for the examination under magnification of a selected generally planar area within the cornea of an eye, said microscope comprising a lens system including a converging lens and an objective lens, observation means, opaque masking means positioned in a plane normal to the optical axis of said microscope between said lens system and said observation means, said masking means including first and second spaced parallel linear slit portions extending therethrough and disposed at opposite sides of said optical axis, means for oscillating said masking means in said plane in a direction normal to the length of said slit portions at a desired rate, illuminating means for directing a beam of light through said first slit portion, said converging lens and said objective lens, to illuminate a narrow elongate area within the cornea of an eye positioned behind said objective lens on one side of said masking means, said observations means being positioned on the other side of said masking means to receive light reflected from said elongate area and passing through said objective and converging lenses and said second slit portion in the direction of said optical axis of said microscope.

2. Apparatus in accordance with claim 1 including means for oscillating said masking means at a rate in excess of the image retention rate of the human eye.

3. Apparatus in accordance with claim 1 and including target screen means for recovering the image passing through said second slit portion.

4. Apparatus in accordance with claim 3 wherein said target screen means comprises a photo-sensitive surface.

5. Apparatus in accordance with claim 4 wherein said photo-sensitive surface comprises the input surface of a photo-intensifier tube.

6. Apparatus in accordance with claim 1 and including means for focusing said microscope at a preselected area within the cornea.

7. Apparatus in accordance with claim 1 wherein said mask oscillates at the rate of about 500 cycles or more per second.

8. Apparatus in accordance with claim 1 wherein the width of said first slit is about 1 mm, and the lateral excursion of said slits is between about 5 to 7 millimeters.

9. Apparatus in accordance with claim 8 wherein said slits are spaced apart from about 16 to 20 millimeters.

* * * * *